United States Patent [19]

Theoharides

[11] Patent Number: 5,994,357

[45] Date of Patent: Nov. 30, 1999

[54] METHOD OF TREATMENT FOR INTERSTITIAL CYSTITIS

[76] Inventor: Theoharis C. Theoharides, 14 Parkman St. #2, Brookline, Mass. 02146

[21] Appl. No.: 08/351,883

[22] Filed: Dec. 8, 1994

Related U.S. Application Data

[63] Continuation of application No. 08/037,668, Mar. 24, 1993, abandoned, which is a continuation of application No. 07/788,176, Nov. 5, 1991, abandoned.

[51] Int. Cl.$^6$ ........................ A61K 31/495; A61K 31/445
[52] U.S. Cl. ............................... 514/255; 514/324
[58] Field of Search ...................... 514/255, 324

[56] References Cited

U.S. PATENT DOCUMENTS 4,594,351  6/1986  Scott ........................ 514/320

OTHER PUBLICATIONS

Grupe et al, Agents Actions Suppl., AAS (Trends Inflammation Res. 2), pp. 273–287, 1982.

Grupe et al 98 CA: 27515 G 1983.

Merck Manual of Diagnosis & Therapy 14$^{th}$ Ed 1982 pp. 1569–1570.

Tozzi et al. 82 CA:68235d 1975.

Engel et al. 115 CA: 142251z 1990.

Coulie et al. 115 CA 421f 1991.

Nouakova et al. 107CA: 91379x.

The Merck Manual of Diagnosis & Therapy 14$^{th}$ ed.

Grupe et al 98 CA:27515 G 1983.

*Primary Examiner*—Russell Travers
*Attorney, Agent, or Firm*—Foley & Lardner

[57] ABSTRACT

A method of treating patients suffering from interstitial cystitis comprising the administration to such patients of an inhibitor of neurohormonal activation of mast cell secretion selected from the group of histamine-1 receptor antagonists consisting of azatadine, azelastine, cetirizine, hydroxyzine and ketotifen, by oral, parenteral, transmucosal, and transdermal routes of administration.

16 Claims, No Drawings

METHOD OF TREATMENT FOR INTERSTITIAL CYSTITIS

This application is a continuation of application Ser. No. 08/037,668, filed Mar. 24, 1993, now abandoned, which is a continuation of application Ser. No. 07/788,176, filed Nov. 5, 1991, now abandoned.

BACKGROUND OF THE INVENTION

This invention relates to a method of treatment for interstitial cystitis. More particularly, this invention is directed to the administration of an inhibitor of neurohormonal activation of bladder mast cell secretion as a methods of treatment for interstitial cystitis.

Interstitial cystitis is a urologic condition of unknown etiology that predominantly (90%) affects young and middle-aged females although men and children can also be affected. It is characterized by irritative voiding symptoms, symptoms of urinary urgency, frequency, dysuria, nocturia, and suprapubic or pelvic pain related to and relieved by voiding. A great number of interstitial cystitis patients also experience headaches, gastrointestinal and skin problems which suggest that interstitial cystitis may represent the end organ (bladder) response of a systemic condition affected by many heterogeneous stimuli triggering a common denominator, the mast cell.

The ulcerative form of the disease is uncommon, accounts for ten percent (10%) of cases and is associated with a reduced bladder capacity and the presence of ulcers and scars. The more common form of the disease is the early or non-ulcerative variety associated with normal bladder capacity and an absence of ulcers. These two forms of the disease may have different etiologies and pathologic characteristics. Symptoms of interstitial cystitis are usually present for many years before diagnosis and they usually peak and stabilize within a few years of diagnosis. Progression of the disease often leads to social and emotional crippling. The pain and frequency may interfere with an individual's ability to work and to socialize, and the nocturia may lead to chronic loss of sleep.

The pathology and pathogenesis of interstitial cystitis have not been clearly elucidated. Theories proposed include infection, vascular obstruction, autoimmunity, inflammatory, neurogenic and endocrine causes. The role of the mast cell in the bladder wall and the bladder surface protective glycosaminoglycan (GAG) layer are current areas of research interest. Recent evidence indicates that bladder mast cells may be activated without necessarily an increase in numbers. Histamine and other mediator release in the bladder wall of interstitial cystitis patients may be a pathogenetic mechanism for the causation of the disease. In spite of the description of increased numbers of mast cells in the bladder wall, there is no agreement regarding whether the mast cell is a consequence of interstitial cystitis or a pathogenetic factor in its causation. However, it appears that mast cells are uniformly activated and have secreted their mediators.

Past treatments for interstitial cystitis have included the administration of antihistamines, sodium pentosanpolysulfate, dimethylsulfoxide, steroids, tricyclic antidepressants and narcotic antagonists. However, these methods have not been successful (Sant, G. R. Interstitial cystitis: pathophysiology, clinical evaluation and treatment. *Urology Annal* 3:171–196, 1989).

The histamine-1 receptor antagonist, pyribenzamine, was first reported in 1958 (Simmons, J. L. and Bunce, F. L. On the use of an antihistamine in the treatment of interstitial cystitis. *American Surgery* 24:664–667, 1958) for use in the treatment of interstitial cystitis. The oral administration of 50 mg of pyribenzamine three times daily was said to produce some symptomatic improvement. However, the duration of the response was variable and this work was never duplicated later.

Oral sodium pentosan polysulfate (Elmiron) has been used in the clinical treatment of interstitial cystitis (Mulholland, S. G. Hanno, P., Parsons, C. L., Sant, S. R, Staskin, D. R. Pentosan polysulfate sodium for therapy of interstitial cystitis. *Urology* 35:552–558, 1990). This compound is a synthetic analogue of a sulfonated glycosaminoglycan, which is the natural compound found in the surface mucin of the bladder mucosa. In interstitial cystitis this protective mucin layer appears to be lost. Oral or intravesical administration of this preparation has been said to replace the protective surface mucin. A disadvantage of this type of treatment is that the drug must be taken numerous times per day because of its short duration. Another disadvantage is that the dosage administered must be high because only a small amount of the drug will reach the site of treatment, since it is primarily liver-metabolized.

Intravesical injections of dimethylsulfoxide (DMSO) have also been used to treat interstitial cystitis (Sant, G. R. Intravesical 50% dimethyl sulfoxide (RIM50-50) in treatment of interstitial cystitis. *Supplements to Urology* 29:17–21, 1987). This method of treatment involves extreme discomfort and inconvenience because it requires the anesthetization and catheterization of the urethra. Most patients experience a garlic-like breath odor and a similar taste in their mouths due to pulmonary excretion of a small percentage of the DMSO as dimethyl sulfide. Bladder spasms and irritability may be experienced with DMSO treatment, as well as urethral burning during voiding which necessitates treatment with oral anticholinergics.

Steroids have been used both intravesically and systemically because their anti-inflammatory action reduces bladder wall inflammation. The improvements obtained with steroid treatment are short-lived, many patients relapse and side effects, such as fluid retention and osteoporosis are common. The unpredictable response and the risk of side effects from prolonged therapy limit the use of steroids.

Tricyclic antidepressants have recently been used to treat patients with interstitial cystitis with about 30% responding. However, patients treated with amitriptyline, the only tricyclic on which data are available, have experienced troublesome side effects such as hypotension, tachycardia, anxiety, or palpitations (Hanno, P. M., Buehler, J., Wein, A. J. Use of amitriptyline in the treatment of interstitial cystitis. *Journal of Urology* 141:846–848, 1989).

Also utilized in the past have been the subcutaneous and intravesical injection of heparin, intravesical injection of silver nitrate and bladder distension. The inconvenience and the potential side effects of these methods do not make them acceptable therapeutic approaches. Therefore, the need exists for a method of treatment of interstitial cystitis that is safe and effective, which need is met by the method of the present invention.

U.S. Pat. No. 4,268,518 (May 19, 1981) discloses that compounds related to 1,3-bis (2-carboxy chromon-5-yloxy)-2-hydroxypropane may be used for the treatment of cystitis in general. However, such compounds do not inhibit secretion from mucosal mast cells (Pearce, F. L., Befus, A. D., Gauldie, J., Bienenstock, J. Effects of antiallergic compounds on histamine secretion by isolated intestinal mast cells. *Journal of Immunology* 126:2481–2486) which are an important component of the pathophysiology of interstitial cystitis. Moreover, such compounds do not block neurohormonal activation of mast cell secretion.

U.S. Pat. No. 4,877,791 (Oct. 21, 1989) discloses the daily administration to patients suffering from interstitial cystitis of the narcotic antagonists, nalmefene or naltrexone. The disadvantages of utilizing narcotic antagonists in the treatment of interstitial cystitis are: a) that they may block mast cell activation by only one trigger (endorphins) not operating in this disease, b) will cause dysthymia, which is characterized by lack of pleasure appreciation and sensation, c) blockade of endogenous opioids (endorphins) which help alleviate the pain and d) inability to use opioids (eg. morphine or demerol) for additional treatment of pain associated with IC. In other words, long-term therapy may lead to more pain.

SUMMARY OF THE INVENTION

To obviate the disadvantages associated with the methods of treatment for interstitial cystitis presently existing, the present invention employs the administration of an inhibitor of neurohormonal activation of mast cell secretion. More specifically, the invention herein relates to a method of treating a patient suffering from interstitial cystitis comprising the administration of a histamine-1 receptor antagonist with mast cell inhibitory action selected from the group consisting of azatadine, azelastine, hydroxyzine and ketotifen.

These agents have the ability to inhibit secretion from bladder mast cells which are activated in interstitial cystitis by neurohormonal triggers. In this way, mast cells do not secrete any of the noxious chemicals which participate in the pathophysiology of interstitial cystitis. In addition, these molecules have anti-cholinergic activity which reduces polyuria and frequency so prominent in interstitial cystitis. Finally, these molecules are soluble in aqueous media permitting easy administration and are free of any serious side effects.

DETAILED DESCRIPTION OF THE INVENTION

This invention is directed to a method of treating interstitial cystitis by the administration of an inhibitor of neurohormonal activation of mast cell secretion. In the context of this disclosure, the following terms shall be defined as follows unless otherwise stated.

"Inhibitor of neurohormonal activation of mast cell secretion" refers to any substance or group of substances, devoid of any psychotropic effects which prevent the stimulation of mast cell secretion by hormones or molecules produced by nervous tissue. Whether or not a pharmacologically active substance is an inhibitor of neurohormonal activation of mast cell secretion can be determined by using the following procedure: Mast cells purified from peritoneal cavities of rats and stimulated by a neuropeptide, such as somatostatin (Theoharides, T. C. and Douglas, W. W. *Endocrinology* 102:1637–1640, 1978), or rat brain slices stimulated by substance P in special perfusion chambers (Dimitriadou, V., Buzzi, M. G., Moskowitz, M. A. and Theoharides, T. C. *Neuroscience* 44:27–39, 1991) or rat bladder mast cells stimulated by carbachol in special perfusion chambers (Theoharides, T. C. and Sant, G. R. *Seminars Urology* 9:74087, 1991) will first be stimulated with concentration of the agents to be tested ranging from 0.1 μmol/L-to-100 μmol/L of solution for varying amounts of time at 37° C. to determine their ability to inhibit subsequent mast cell secretion as described above.

"Therapeutically effective amount" refers to an amount sufficient to produce inhibition of neurohormonal activation of mast cell secretion at a level of inhibition not less than 20% and preferably greater than 70%.

"Histamine-1 receptor antagonist" refers to a substance or group of substances which bind to the histamine-1 receptor of endothelial cells at a concentration less than $10^{-4}$ M (Molar).

"Degranulation" is, henceforth, defined as the release of any or all mediators from any or all secretory granules, whether in parallel, differentially or selectively. Relevant examples of such responses are vasoconstriction or vasodilation.

I. MAST CELL BIOLOGY

Mast cells are a normal component of the connective and mucosal tissues and play an important role in allergy and inflammation. They are localized in the mucosa and connective tissue, meninges, membranes protecting the brain, the bladder, gastrointestinal mucosa, skin and lung. They are believed to be located there because these tissues are the main entry points for infective organisms and allergens, chemicals which trigger the body's immune response.

Each mast cell contains up to 500 secretory granules, each storing more than 20 potent biological compounds. Mast cells secrete the contents of these granules (i.e., degranulate) when triggered by various specific and non-specific mechanisms.

The compounds secreted by the mast cells following degranulation are known to cause many biological responses which are part of the overall response of the body to invasion by infective organisms (inflammatory response) or allergens.

The degranulation of mast cells in response to various agents is a biological consequence of the activation of one or more receptors which are located on the surface of the mast cell. The best known receptor is immunoglobulin E (IgE), which is involved in allergic reactions. However, there has been recent evidence that neuropeptides, molecules released from neurons in the nervous system and brain, also trigger mast cell degranulation through specific receptors, especially in response to stress. Known neurohormonal triggers include the neuropeptides calcitonin-gene-related peptide (CGRP), neurotensin, peptide Y, somatostatin, substance P and vasoactive intestinal peptide (VIP), neurotransmitters such as acetylcholine (Theoharides, T. C. Mast cells: the immune gate to the brain. *Life Science* 46:607–617, 1990) and female sex hormones such as estradiol and progesterone (Vliagoftis et al. Progesterone triggers selective mast cell secretion of 5-hydroxytryptamine. *Int. Arch. Allery Appl. Immunol.* 93:113–119, 1990). It is, therefore, clearly important to block mast cell secretion in response to neurohormonal stimuli, as well as other triggers, such as, viral and bacterial toxins, drugs such as aspirin, morphine and curare, contrast media used in radiology, extreme cold, radiation, hyperosmotic media and pressure (Theoharides, T. C. and Sant, G. R. Bladder mast cell activation in interstitial cystitis. *Seminars Urology* 9:74–87, 1991).

Compounds released by mast cell degranulation which may be associated with interstitial cystitis include prostaglandins, leukotrienes, histamine, heparin and chemotactic actors, which can cause vasodilation, smooth muscle contraction, inflammation, neural stimulation and pain, as well as proteolytic enzymes (Table 1) which can cause tissue destruction and pain thus explaining many of the symptoms as well as the endoscopic appearance of interstitial cystitis patients.

TABLE 1

Mast Cell Mediators

| Prestored | De Novo |
|---|---|
| Arylsulfatases | Leukotrienes LTB$_4$ |
| Chemotactic factors | Leukotrienes |
| Chymase | Platelet Activation factor (PAF) |
| Cytokines (IL-1,2,3,4,5 & 6, GM-CSF, TNF) | Prostaglandins |
| | Thromboxanes |
| Heparin | |
| Histamine | |
| Kinogenases | |
| Serotonin | |
| Tryptase | |

Histamine and the other mediators are secreted from the granules of mast cells during degranulation. The histamine and other mediators then bind to specific receptors on the surface of endothelial cells on vessels, neurons or other tissues. Vasodilation and chemoattraction permits lymphocytes to leave the circulation and enter the tissue, where they cause additional mast cell degranulation and other inflammatory noxious responses. The process of degranulation continues, eventually involving many mast cells. It is important to note that common antihistamines act only after the secretion of histamine, one of the many mediators necessary for delayed hypersensitivity reactions (the delayed response) which is required for inflammation to occur. It is believed that mast cell chemicals such as histamine and prostaglandins dilate local vessels permitting blood-borne leukocytes to enter the affected organ and create the inflammation, leading to tissue destruction and fibrotic changes. Secondary reactions from mast cell and leukocyte chemicals, along with the tissue destruction itself, cause the pain associated with these conditions. Table 2 lists endogenous pain-producing substances released from mast cells.

TABLE 2

Endogenous Pain-Producing Chemicals Secreted From Mast Cells

Adenosine Phosphates (AAP, ADP, ATP)
Bradykinin
Histamine
5-Hydroxytryptamine (serotonin)
Leukotrienes
Lymphokines
Potassium
Prostagladins
Tumor necrosis factor It has been found that the administration of a therapeutically effective amount of an inhibitor of neurohormonal activation of mast cell secretion can be used in the treatment of interstitial cystitis. The following histamine-1 receptor antagonists have been found by the applicant to inhibit neurohormonal activation of bladder mast cell secretion and are suitable for use in the practice of this invention: azatadine, azelastine, cetirizine, hydroxyzine and ketotifen. Although applicant does not intend to be bound by any theory or proposed mechanism of operation, it is believed that these polycyclic histamine-1 receptor antagonists interfere with the ability of the mast cell to fuse the perigranular membranes to the surface membrane, thus preventing degranulation. More specifically, as regards to hydroxyzine, the characteristics of this drug which are useful in alleviating interstitial cystitis symptoms are listed in Table 3 below.

TABLE 3

Unique Characteristics of Hydroxyzine

Hydroxyzine is a tricyclic, piperazine histamine-1 receptor antagonist
Hydroxyzine inhibits secretion from stimulated bladder mast cells
Hydroxyzine inhibits neuropeptide release from neurons stimulated by high K$^+$
Hydroxyzine has strong anticholinergic properties decreasing frequency
Hydroxyzine is an anxiolytic which may help alleviate stressful triggers

II. INHIBITORY ACTIVITY ON NEUROHORMONAL ACTIVATION OF MAST CELLS

These compounds can be tested by preincubating mast cells purified from the peritoneal cavity of rats with various concentrations of compound, typically 0.1 $\mu$mol/L to 1,000 $\mu$mol/L, for various times at 37° C. before stimulating mast ctll secretion with a stimulus such as somatostatin (Theoharides, T. C. and Douglas, W. W. Somatostatin induces histamine secretion from rat peritoneal mast cells. *Endocrinology* 102:1637–1640, 1978).

More appropriate to interstitial cystitis, bladder mast cells can be triggered to secrete in situ using slices of rodent bladders in perfusion chambers and measuring secreted chemicals (Theoharides, T. C. and Sant, G. R. Bladder mast cell activation in interstitial cystitis. *Seminars Urology* 9:74–87, 1991).

In addition, compounds which inhibit mast cell degranulation are listed below under class (Table 4).

TABLE 4

Drugs which Inhibit Neurohormonal Activation of Mast Cell Secretion

Anthralinic acid derivatives

N-(3,4-dimethoxycinnamoyl) anthranilic acids
Antibiotic

Cyclosporin A
Antihormones

Tamoxifen
Arachidonic acid metabolites

Leukotriene D$_4$
Lipoxin B
Phospholipase A$_2$
Prostaglandin D$_2$
Prostaglandin E$_1$
Prostaglandin E$_2$
ATPase inhibitors Ethacrynic acid
Ouabain
Calcium entry blockers Diltiazem
Nifedipine
Nimodipine
Verapamil
Histamine-1 receptor antagonists Piperidines Azelastine
Azatadine
Burfroline
Doxantrozole

TABLE 4-continued

Drugs which Inhibit Neurohormonal Activation of Mast Cell Secretion

Forskolin
Ketotifen
Lodoxamide tromethamine
Loperamide
Myricetin
Oxatomide
Pizotifen
Proxicromil
Terfenadine
Piperazines 1-(5-Isoquinolinylsulfonyl)-2-methylpiperazine
1-(1-Hydroxy-5-isoquinolinylsulfonyl)piperazine
Cetirizine
Etodroxizine
Hydroxyzine
$N^1$-substituted benyhydryl
Tertiary alkylamine Pyrilamine
Peptides L-Asp-Ser-Asp-Pro-Arg
Forssman antibody
Lymphocyte inhibitory factor (LIF)
Phenothiazines Prochlorperazine
Thioridazine
Trifluoperazine
Polyamines Spermidine
Spermine
Quinoline derivatives 1,3-oxazolo[4,5-h]quinolines
2-Carboxypyrimidoquinolines
3-Aminoquinolines
6-(methylamino)-4-oxo-10-propyl-4H-pyrano [3,2-g] quinolin-2, 8 dicarboxylate
9-ethyl-6, 9-dihydro-4, 6-dioxo-10 propyl-4H-pyrano [3,2-g] quinolin-2, 8 dicarboxylate
Ethoxyethyl 5-chlorobenzoxazole-2-carboxylate
5-Chlorobenzoxazole-2-carboxylic acid
Thiophene derivatives 1-methyl-2(1,3,4-oxadiazol-2(3H)-one-5-yl) Benzimidazolel (RH3288)
Toxins Diptheria toxin
Pertussis toxin The inhibitor of neurohormonal activation of mast cell secretion is administered in a therapeutically effective amount. The dosage range for therapeutic effectiveness can be determined by reference to standard aforementioned laboratory tests for inhibition of mast cell activation and by the dosages used for such agents in other conditions.

The inhibitor can be administered by known methods for drug administration, typically in connection with a pharmaceutically acceptable carrier. It can be administered alone or in conjunction with other therapeutic agents, provided those therapeutic agents do not directly or indirectly promote mast cell secretion.

The therapeutically effective dose of the inhibitor of neurohormonal activation of mast cell secretion can be determined by its $ID_{20}$, which is defined as the dose necessary to cause 20% inhibition of mast cell secretion when applied to cultured mast cells. The $ID_{20}$ of the histamine-1 receptor antagonists of the present invention which inhibit bladder mast cell secretion as defined by the inventor is as follows (Table 5):

TABLE 5

Inhibition of Mast Cell Secretion by Antihistamines

| H-1 Receptor Antagonist With Mast Cell Inhibitor Activity | $ID_{20}$ for Histamine Release from Rat Bladder Mast Cells In Vitro |
|---|---|
| Azatadine | $10^{-6}$ M |
| Azelastine | $10^{-6}$ M |
| Hydroxyzine | $5 \times 10^{-5}$ M |
| Ketotifen | $10^{-5}$ M |

$ID_{20}$ = inhibitory dose causing 20% inhibition
M = molar concentration

III. PREFERRED EMBODIMENT

The dosage of inhibitor of neurohormonal activation of mast cell secretion for use in mammals can be calculated from the effective dose data by experimental selection especially extrapolating the moles per liter set forth above directly to moles per kilogram of subject to be treated. In general, the $ID_{50}$ is tested at 0.05 mg to 10 mg per kilogram body weight of the mammal, equivalent to about 4 to 800 milligrams per 80 kilograms of weight.

Immediately suitable mast cell degranulation inhibitors for use in this invention are set forth on the foregoing Table 5, along with the concentrations of each agent required for inhibition.

The inhibitor of neurohormonal activation of mast cell secretion of this invention are typically administered as pharmaceutical compositions containing pharmaceutically acceptable carriers combined with the active agent. Such compositions may be prepared from conventional materials by procedures well known in the art.

The compositions of this invention may be adapted for oral or parenteral administration, as well as for administration through mucous membranes such as intranasal, sublingual, buccal, rectal, as well as transdermal.

Forms suitable for oral administration include solid forms such as tablets, dispersible powders, granules, capsules and liquid or semi-liquid forms such as syrups, elixirs and suspensions.

Compositions for oral use contain one or more conventional adjuvants, such as sweetening agents, flavoring agents, coloring agents and preserving agents, in order to provide a presentable and palatable preparation. Tablets may contain the active ingredients in a mixture with conventional pharmaceutically acceptable excipients. These include inert carriers, such as calcium carbonate, sodium carbonate, lactose, and talc; granulating and disintegrating agents, such as starch and alginic acid; binding agents such as starch, gelatin acacia; and lubricating agents, such as magnesium stearate, stearic acid and talc.

Tablets may be uncoated or coated by known techniques to delay disintegration and absorption in the gastrointestinal tract thereby providing a sustained action over a longer period of time. Similarly, suspensions, syrups and elixirs may contain active ingredients in mixture with any of the conventional excipients utilized in the preparation of such compositions. This includes suspending agents such as methylcellulose, tragacanth and sodium-alginate wetting agents such as lecithin, polyoxyethylene stearate or polyoxyethylene sorbitan monoleate; and preservatives. Capsules may contain the active ingredients alone or in admixture with an inert solid carrier, such as calcium carbonate, calcium phosphate or kaolin. These pharmaceutical compositions may contain up to 90% of active ingredients in combination with the carrier or adjuvant. Preferably, the compounds are put in unit dosage forms particularly for oral administration. Such forms may contain the active ingredient separately, for example in separate layers. Oral administration is preferred if the inhibitor of neurohormonal activation of mast cell secretion is orally active.

The inhibitors can be administered in sustained release form or in divided dosages. In the case of inhibitors which are substantially destroyed or deactivated upon oral administration, or where a more immediate response is desired or prolonged duration of activity is desired, the inhibitor of this invention can also be administered transdermally or via other body membranes such as rectally, sublingually or buccally. Similarly, the compositions of this invention are administered by those routes with carriers known for such administration.

For parenteral routes, the inhibitor of neurohormonal activation of mast cell secretion maybe administered as: subcutaneous, intramuscular, intravenous and intravesical routes.

The inhibitor of neurohormonal activation of mast cell secretion can be administered in the form of the active agent itself or as a pharmaceutically acceptable salt of the active agent. The term "pharmaceutically acceptable salt" means a non-toxic, substantially non-irritating salt of the compound used. Typical salts include those containing a cation, which is an alkali metal or alkaline earth metal, such as sodium, potassium, calcium, magnesium or ammonium. Suitable cations for the salt include sulphate, phosphate, tartrate and citrate. Other acceptable salts are those with non-toxic organic acids, such as fatty acids of one to six carbon atoms, or molecules such as pamoate.

The following three examples are illustrative only and should not be construed as limiting the invention in any way. Those skilled in the art will appreciate that variations are possible which are within the spirit and scope of the appended claims. Table 6 summarizes the clinical data available at the present (including the examples listed below).

IV. EXAMPLES

Example 1

A twenty-nine-year-old female (CM) suffering from interstitial cystitis for two years had been treated with conventional methods and amitriptyline with limited success. She was administered a 75 mg oral dose of hydroxyzine pamoate per day. After 5 days the burning sensation upon voiding and sharp pelvic pain disappeared. In two months, the extreme tenderness from her chest area to pelvic area also disappeared. After about 10 to 12 weeks frequency was eliminated. She "felt 100% normal" and slowly resumed a diet, including spicy foods and bananas, which she could not tolerate before. Upon discontinuing administration of hydroxyzine pamoate symptoms reappeared within 24 hours or less. After one year of treatment, the female subject takes 50 mg and 25 mg of hydroxyzine pamoate, respectively, on alternating days, with continued 100% success.

Example 2

This 32 year old female (JP) was diagnosed with interstitial cystitis in March 1989. Six DMSO treatments and one heparin treatment provided very limited relief. Her symptoms included constant burning in the bladder, pain at the connection of the buttocks with the upper legs and painful sexual intercourse. She could not sleep although her need to urinate was only about four times per night. Sitting on "blue ice" packs wrapped in a cloth provided some relief from the buttock pain and the burning. Amitriptyline (25 mg) enabled her to sleep some. However, many foods still brought severe symptoms. Since she started taking hydroxyzine-HCl in March 1991, the burning has subsided significantly, the buttock pain is reduced and she can eat some offending foods in small quantities. Sexual intercourse is no longer associated with severe bladder pain. She reports that hydroxyzine-HCl has definitely improved the quality of her life.

Example 3

This is a 35 year old female (EMG) who experienced increasing problems over the last 10 years until it became difficult to function as a nurse, mother and wife. After an A&P repair, hysterectomy and continued pain and frequency, she was finally diagnosed with interstitial cystitisand ultimately treated with DMSO with fairly good improvement. She had not received any treatment since February 1990 and was experienceing a flare up of symptoms when she tried hydroxyzine-HCl. She has used this medication daily since May 1990 with remarkable control of symptoms which had plagued her life for the last several years. She can now maintain almost total bladder comfort with 25 to 50 mg of this drug daily. On 2 or 3 occasions she attempted to withdraw the use of this drug with a definite increase in interstitial cystitissymptoms.

Table 6 summarizes the data available on nine patients, three of whom were described in the previously listed examples.

TABLE 6

| Clinical Data on Hydroxyzine in IC |
| --- |
| Patients: 9 females (26–55 years/old) |
| Duration of symptoms: 7 ± 6 years |
| Duration of treatment: mean time 8 ± 5 months |
| Amount: 25 mg twice - three times/day × 8 months |
| Alternate: 25 mg every other day past 8 months |
| Results: 80–100% relief from frequency, dysuria, pain |
| Problems: Mild sedation, weakness × 1 week |

The invention being thus described, it will be obvious that the same may be varied in many ways. Such variations are not to be regarded as a departure from the spirit and scope of the invention, and all such modifications are intended to be included within the scope of the claims.

What is claimed is:

1. A method of treating non-ulcerative non-inflammatory interstitial cystitis in a patient identified as suffering from interstitial cystitis comprising the administration to the patient of a therapeutically effective amount of hydroxyzine or a salt thereof.

2. A method according to claim 1 wherein hydroxyzine or a salt thereof is administered to the patient in an oral dosage form comprising a dispersible powder, a tablet, capsule, liquid or semi-liquid suspension.

3. A method according to claim 1 wherein hydroxyzine or a salt thereof is administered to the patient parenterally.

4. A method according to claim 3 wherein hydroxyzine or a salt thereof is administered to the patient by the subcutaneous, intramuscular, intravenous, intravesical, transmucosal or transdermal routes.

5. A method of treating non-ulcerative interstitial cystitis in a patient identified as suffering from interstitial cystitis comprising the administration to the patient of a therapeutically effective amount of ketotifen or a salt thereof.

6. A method according to claim 5 wherein ketotifen or a salt thereof is administered to the patient in an oral dosage form comprising a dispersible powder, a tablet, capsule, liquid or semi-liquid suspension.

7. A method according to claim 5 wherein ketotifen or a salt thereof is administered to the patient parenterally.

8. A method according to claim 7 wherein ketotifen or a salt thereof is administered to the patient by the subcutaneous, intramuscular, intravenous, intravesical, transmucosal or transdermal routes.

9. A method of treating interstitial cystitis in a patient identified as suffering from interstitial cystitis, comprising administration to the patient of a therapeutically effective amount of hydroxyzine or a salt thereof.

10. The method of claim 9, wherein said interstitial cystitis is characterized by neurohormonal activation of bladder mast cell secretion.

11. The method of claim 10, wherein said hydroxyzine or a salt thereof is administered to the patient in an oral dosage form comprising a dispersible powder, a tablet, capsule, liquid or semi-liquid suspension.

12. The method of claim 10, wherein said hydroxyzine or salt thereof is administered to the patient parenterally.

13. A method of treating interstitial cystitis in a patient identified as suffering from interstitial cystitis, comprising administration to the patient of a therapeutically effective amount of ketotifen or a salt thereof.

14. The method of claim 13, wherein said interstitial cystitis is characterized by neurohormonal activation of bladder mast cell secretion.

15. The method of claim 14, wherein said ketotifen or a salt thereof is administered to the patient in an oral dosage form comprising a dispersible powder, a tablet, capsule, liquid or semi-liquid suspension.

16. The method of claim 14, wherein said ketotifen or salt thereof is administered to the patient parenterally.

* * * * *